United States Patent [19]

Shearer et al.

[11] Patent Number: 5,507,173

[45] Date of Patent: Apr. 16, 1996

[54] GAS ANALYZER UTILIZING CANCELLATION OF PARALLEL MICROWAVE BEAMS

[76] Inventors: Robert M. Shearer; Dyana Y. Shearer, both of 2104 Wagon Gap Dr., Round Rock, Tex. 78681

[21] Appl. No.: 269,204

[22] Filed: Jun. 30, 1994

[51] Int. Cl.$^6$ ................................................ G01N 22/00
[52] U.S. Cl. ........................ 73/23.2; 250/330; 324/639; 324/636
[58] Field of Search .......................... 73/23.2; 324/636, 324/637, 639; 250/330

[56] References Cited

U.S. PATENT DOCUMENTS

| | | | |
|---|---|---|---|
| 4,390,785 | 6/1983 | Faulhaber et al. | 250/330 |
| 4,894,603 | 1/1990 | Berger et al. | 324/639 |
| 4,896,097 | 1/1990 | Berger et al. | 324/639 |
| 4,952,895 | 8/1990 | Quan | 333/121 |
| 5,057,782 | 10/1991 | Brown et al. | 324/639 |
| 5,252,827 | 10/1993 | Koga et al. | 250/281 |

*Primary Examiner*—Hezron E. Williams
*Assistant Examiner*—J. David Wiggins

[57] ABSTRACT

A method for analyzing a gaseous mixture by means of microwave absorption including the steps of: generating microwave energy of at least one frequency known to be absorbed by the component of interest of the gaseous mixture for the presence of one specific gas component; transmitting two beams of the microwave energy simultaneously to a measuring cell and to a reference cell, both cells containing none of the specific gas component of interest; recombining the microwave energy through the matching arms of a waveguide "magic" tee with an "H" arm and an "E" arm; adjusting the phase and amplitude of the reference or measuring beam signals of microwave energy until a null is detected at the "E" arm of the waveguide "magic" tee and all microwave energy is detected at the "H" arm of the microwave tee; allowing the measuring cell to fill with the gaseous mixture to be analyzed; correlating the energy detected at the "H" arm to the concentration of the gaseous component of interest, according to Beer's law. Also provided is an apparatus which may be used in conjunction with this method.

11 Claims, 2 Drawing Sheets

5,507,173

GAS ANALYZER UTILIZING CANCELLATION OF PARALLEL MICROWAVE BEAMS

CROSS REFERENCE TO RELATED APPLICATIONS

This application represents a continuation and completion of the work described in Disclosure Document 324349 as received at the U.S. Patent and Trademark Office on Jan. 25, 1993.

BACKGROUND OF THE INVENTION

The invention relates to a method of analyzing gaseous media by means of microwave absorption, particularly for the determination of gas concentrations, wherein a microwave is generated at least one frequency. The invention also relates to an apparatus for analyzing gaseous media by means of the absorption of microwaves, particularly for a determination of concentrations, primarily for implementing the method and comprising at least one microwave transmitter, at least one measuring cell, at least one reference cell, at least one detector, at least one waveguide "magic" tee, amplifying and display devices for the measurement signal as well as a control device for the microwave transmitter.

It is known to analyze gaseous media, possibly also after conversion of a solid or a liquid into the gaseous state, by absorption of microwaves within certain characteristic frequency ranges by the excitation of rotational transitions in molecules of the media to be examined. If necessary to reduce the line width, the examination may take place in the low pressure range. The absorption of microwave energy by the gaseous component of interest is detected when the absorption upsets the balance of energy arriving at the waveguide "magic" tee via the measuring and reference cells. Such a process is highly selective, in principle, but does not require prior modifications, such as ionization or chemical reactions, of the substances to be examined.

In the past, examination of the concentration of trace amounts of a particular component of a gaseous mixture, directly by the absorption of microwave energy, has not been practiced due to insensitivity and non-specificity of the methods employed.

Nuclear magnetic resonance and electron paramagnetic resonance methods, as opposed to direct microwave absorption methods have demonstrated useful degrees of sensitivity and specificity, but have the disadvantage of complexity, cost, size, difficulty of operation and maintenance and lack of reliability. These negative attributes are evidenced by the absence of commercially available gas analyzers based on microwave methods.

SUMMARY OF THE INVENTION

An important object of this invention is to provide signals which represent the sum and difference of two parallel, coherent microwave beam energies, from a single source. One energy is passed through an appropriately constructed waveguide sample cell, the other through a similarly constructed reference cell of equal length.

Another important object is that a means is provided for selectively removing the gaseous component of interest from the gaseous mixture in the reference cell, said gaseous mixture being otherwise essentially identical to that contained in the sample cell.

Yet another object of this invention is that an intermittent flow control means (solenoid valve) is provided for periodically allowing both the sample and reference cells to fill with the same gaseous mixture that has had the component of interest removed or converted. During the interval that both cells are filled with an identical gaseous mixture depleted of the gas component of interest, a further object of hulling the difference signal is accomplished by means of a vector modulator(S) and/or separate phase and amplitude modulators.

A further object of this invention allows, if necessary, that the reference and sample cells be allowed to operate at reduced, equal pressures to reduce the effects of collision intermolecular broadening the absorption spectrum. Additionally, at either reduced or ambient pressure, said pressure is quantified by provided means for use in computing the concentration of the component of interest according to Beer's law.

The forgoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF PREFERRED EMBODIMENTS

Figure 1:
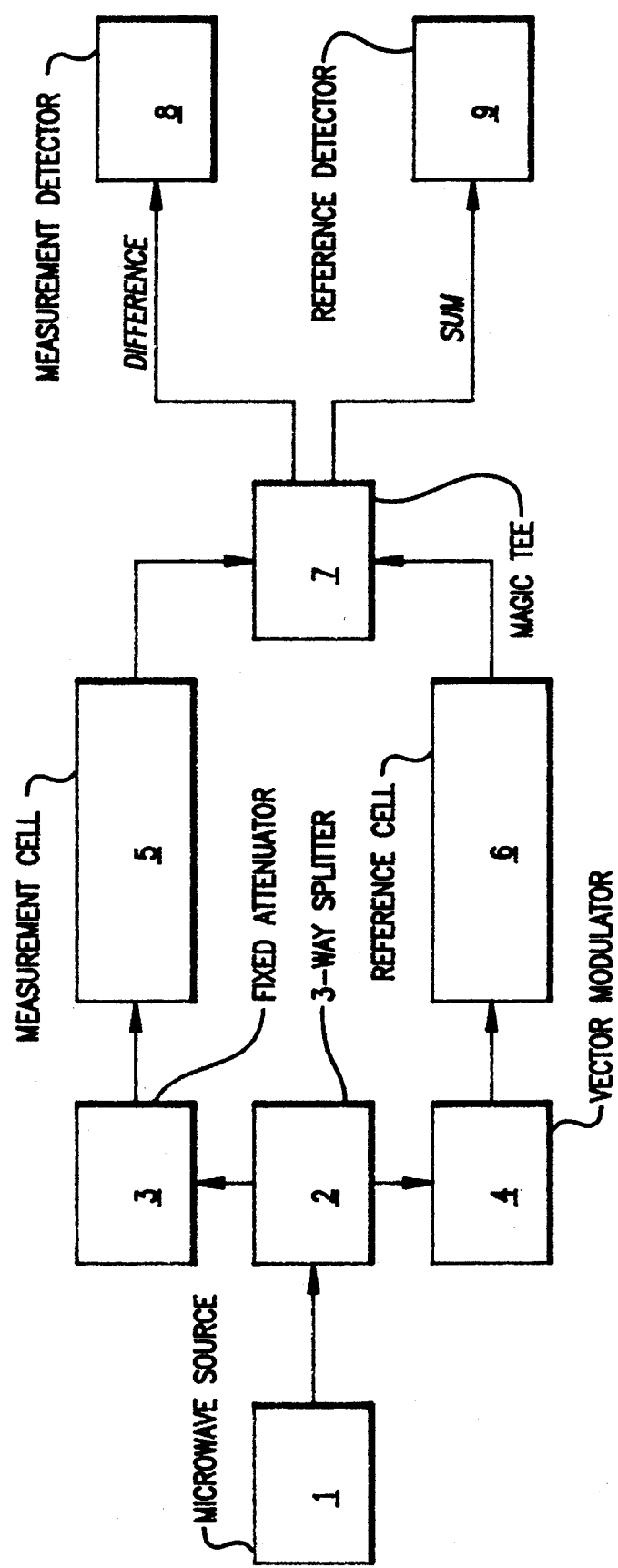
FIG. 1. is a block diagram/schematic representation of a device incorporating the primary objects of the present invention.

Referring to FIG. 1, there is shown in block diagram/schematic form, a device which will accomplish the primary object for which a patent is sought. Said device includes microwave source 1, fixed attenuator 3, power splitter 2, vector modulator 4, measurement cell(waveguide) 6, waveguide "magic" tee 7, measurement detector 8, and reference detector 9. Microwave source 1 is any suitable source of microwave energy, the output of which is able to achieve the desired absorption wavelength, and of which the spurious and noise content within the passband of measurement cell 5 and reference cell 6 is acceptable, typically −50 dBc or less. The power output requirements of microwave source 1 at the absorption frequency are not great, typically −20 dBm to +10 dBm. Power splitter 2 is typically a solid state device with coaxial connectors for the input and outputs, but may, again, be of any suitable construction by which the objects of this application may be obtained, namely to provide a multiple beam forming capability. Fixed attenuator 3 is selected such that the attenuation provided at the absorption frequency is somewhat greater than the nominal insertion loss of vector modulator 4, when said vector modulator is adjusted for minimum attenuation. Vector modulator 4 is any device or combination of devices such that the phase and amplitude of the microwave energy transmitting reference cell 6 may be precisely matched to the microwave energy transmitting measurement cell 5, said match being determined as the condition of no microwave energy detected at measurement detector 8.

Measurement detector 8 and reference detector 9 are typically square-law detectors selected such that the difference and sum signals formed from the two received beams are within the useable, "linear" portion of the respective detector responses. A waveguide "magic" tee 7 has an "E" arm and an "H" arm, which are used together with detectors and associated electronics in a beam combining apparatus such that the system provides suitable means of generating electrical signals representing the vector sum and difference or superposition of two microwave energies.

In operation, the microwave source 1, is first tuned to a frequency absorbed by the gas of interest. Measurement cell 5 and reference cell 6 are allowed to fill with a gaseous mixture from which the gas of interest has been absorbed or chemically converted to another compound. Vector modulator 4 is adjusted, by manual or automatic means as applicable, such that no microwave energy is detected at measurement detector 9. Measurement cell 5 is then allowed to fill with the original gaseous mixture from which the gas of interest has not now been removed. Any microwave energy detected at measurement detector 8 is due and proportional to, the amount of the gas of interest contained in the gaseous mixture. Fixed attenuator 3 is selected such that the microwave beams transitting the reference and measurement cells may be matched at all frequencies.

Figure 2:
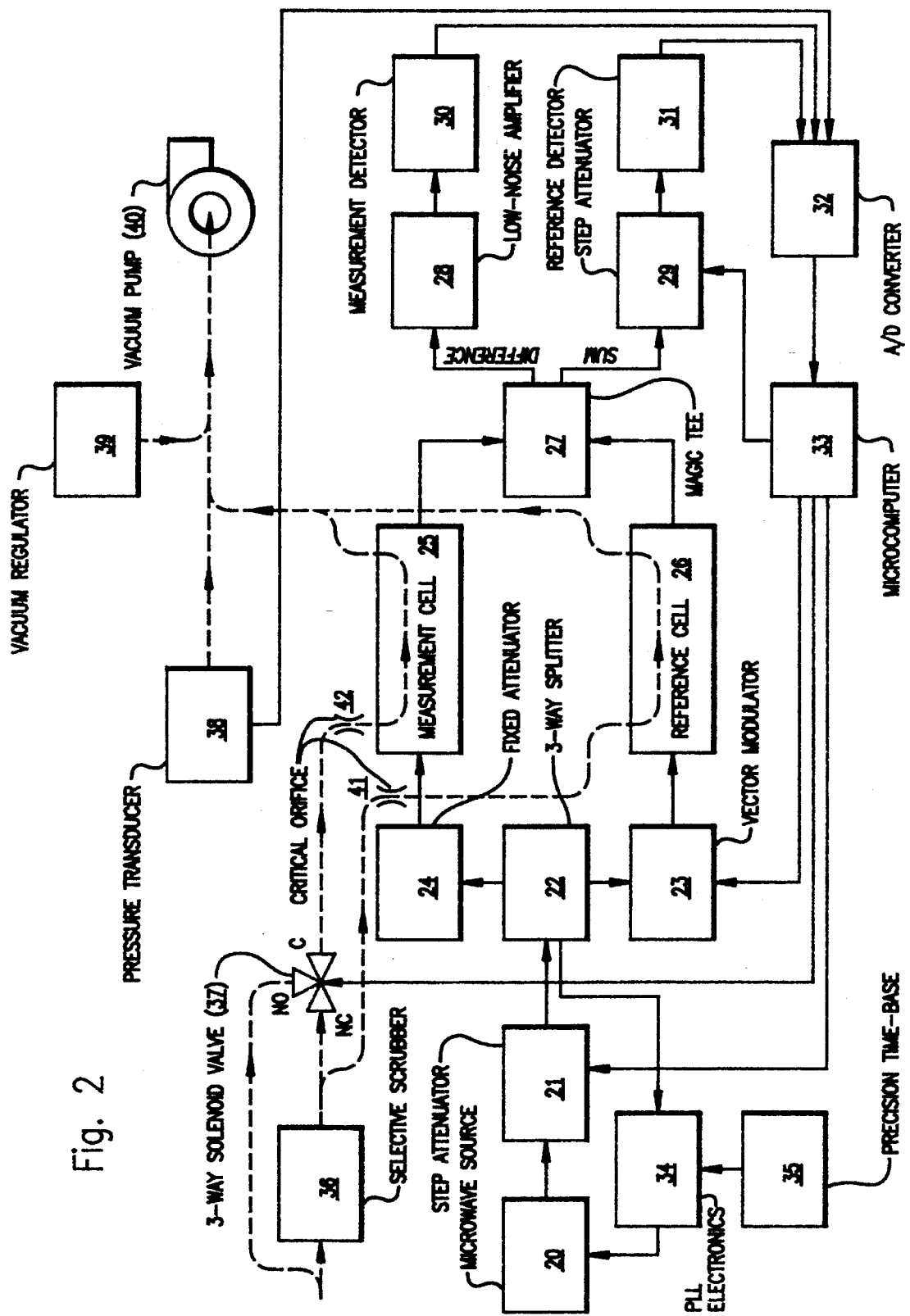
FIG. 2. is a block diagram/schematic representation of a preferred embodiment of a gas analyzer incorporating all features of the present invention.

Referring to FIG. 2, there is shown a preferred embodiment of a gas analyzer utilizing the aforementioned method, as illustrated in FIG. 1. Microwave source 20, fixed attenuator 24, vector modulator 23, measurement cell 25, reference cell 26, waveguide "magic" tee 27, measurement detector 30, and reference detector 31, have identical functions to the counterparts of the same name as described in the preceding description of FIG. 1. Also included are step attenuator 21, phase-lock loop (PLL) electronics 34, precision time base 35, low noise amplifier (LNA) 28, A-D converter 32, microcomputer 33, selective scrubber 36, three-way pneumatic solenoid valve 37, pressure transducer 38, vacuum regulator 39, vacuum pump 40, and critical orifices 41 and 42.

Step attenuators 21 and low noise amplifier 28, also containing a step attenuator, are of the same or similar construction, and may be provided as "function modules", or constructed of discreet components both being well known in the art. The attenuation provided is under control of microcomputer 33, and the attenuation provided would nominally be 0 to −40 dB in 10 dB steps.

PLL electronics 34 represents any of several methods known in the art of generating microwaves of a known frequency as referenced to precision time base 35. Precision time base 35 is required to have long term stability on the order of $1 \times 10^{-8}$. Low noise amplifier 28 is, again, of a conventional design and with features commonly known in the art. A to D converter 32 may be taken to represent as many discreet A to D converters as are necessary to allow continuous conversion of all analog signals required for analyzer operation.

Microcomputer 33 is any such device, known in the art, which is capable of controlling the function, and interpreting the response of the analyzer. Selective scrubber 36 is a device capable of selectively removing the gas of interest from the gaseous mixture analyzed, or converting said gas of interest into another form which does not absorb the same wavelength of microwave energy.

Three-way pneumatic solenoid valve 37, is a device known in the art which when de-energized, allows gases to flow from the NO port to the C port, and when energized, allows gases to flow from the NC port to the C port and is of such materials and construction that the parts, in contact with the gaseous mixture being analyzed will have no chemical effect on said gaseous mixture. Pressure transducer 38 is any suitable means of monitoring the absolute pressure of the gases in measurement cell 25 and reference cell 26, typically an electric strain gauge-type transducer. Vacuum regulator 39 is any device known in the art for regulating the system gas pressure (vacuum) but as shown would be of the type that allows the entry, (post-measurement and reference cell) of ambient air to maintain a constant pressure (vacuum).

Vacuum pump 40 is any device known in the art suitable for transporting the gaseous mixtures being analyzed while at the same time, lowering the system gas pressure (vacuum) to a level such that the effects of collision broadening are sufficiently minimized.

Critical orifices are devices known in the art to be used for the control of gaseous flow, and, if placed at the pneumatic inlets to the reference and measurement cells, will have the second purpose of allowing, in conjunction with vacuum pump 40, the pressure of the gaseous mixture to be reduced.

To operate the device depicted in FIG. 2, microwave source 20 is tuned to a wavelength absorbed by the gas of interest. Three-way solenoid valve 37 is energized, both measurement cell 25 and reference cell 26 are allowed to fill with the gaseous mixture being analyzed, and said gaseous mixture is passed through selective scrubber 36. Sufficient time is allowed for the detector responses to stabilize, and then vector modulator 23 is adjusted by microcomputer 33 until the microwave energy being detected by measurement detector 30 is zero or minimum. Three-way solenoid valve 37 is then de-energized, which allows measurement cell 25 to fill with the gaseous mixture to be analyzed, but without such gaseous mixture passing through the selective scrubber. If the gas of interest is present in the gaseous mixture being analyzed, then the microwave energy passing through measurement cell 25 will be attenuated with respect to that passing through reference cell 26. The energy detected therefore at measurement detector 30 will be proportional, by Beer's law, to the amount of the gas of interest contained in measurement cell 25. This amount may be converted into concentration units if the pressure and temperature of the gaseous mixture is known.

The pressure is given by pressure transducer 38, or may optionally be set and maintained at a known value by vacuum regulator 39, the device of the pressure transducer thereby being unnecessary. Similarly, the temperature of the gases in measurement and reference cells 25 and 26 may be sensor may simply be controlled at a predetermined value. Although not shown, microcomputer 33 contains or is connected to a suitable means of displaying the concentration of the gas of interest.

We claim:

1. We claim a microwave-absorption gas analyzer system for determining concentration of a specific gas in a gaseous mixture which includes: a frequency-controlled source of microwave energy; a power splitter having at least three output beams, said output beams in turn supply energy to at least one measurement cell for providing at least one measurement cell beam signal, at least one reference cell for providing at least one reference cell beam signal, and also supply a phase-locked loop that links said power splitter to the microwave energy source where said loop includes means for providing a precision frequency reference; equal length measurement and reference cells; a means of matching the phase and amplitude of the signals emerging from the measurement and reference cells; a means of selectively removing the gas of interest from the gaseous mixture being analyzed for use in the reference cell; a means of periodically selectively removing the gas of interest from the gaseous mixture being analyzed for use in the measurement cell; a means of continuously drawing the gaseous mixture being analyzed through the reference cell, the measurement cell, and the means of selectively removing the gas of interest; a means of deriving signals representative of the sum and difference superposition of the measurement cell beam and reference cell beam signals; a means of adjusting the level and phase of the measurement and/or reference beam signals such that a null is obtained by the difference superposition during intervals when the gas of interest has been selectively removed from the gaseous mixture in the measurement cell; a means, if necessary for the gas being analyzed, of reducing and equalizing the pressures of the gaseous mixtures contained in the reference and measurement cells; a means of measuring the pressure of the gaseous mixture in the cells; a means of measuring the temperature of the gaseous mixtures in the cells; a means of computing, by Beer's Law, from the sum superposition, difference superposition, temperature, and pressure signals, the concentration of the gas of interest in the gaseous mixture being analyzed.

2. We claim the microwave gas analyzer recited in claim 1 in which the means of deriving said sum and difference signals is a so called "magic" waveguide tee.

3. We claim the microwave gas analyzer recited in claim 1 in which the measurement and reference cells are internally coated and windowed with Teflon.

4. We claim the microwave gas analyzer recited in claim 1 in which the means of achieving a null in the superposition of the measurement and reference beam signals is a so called vector modulator.

5. We claim the microwave gas analyzer recited i claim 1 in which the source of microwave energy is a yttrium-iron-garnet (YIG) controlled oscillator.

6. We claim the microwave gas analyzer recited in claim 1 in which the means of selectively removing the gas of interest is a selective scrubber that is used to provide the atmosphere in the reference cell.

7. We claim the microwave analyzer recited in claim 1 in which a pneumatic network consisting of a solenoid valve and the appropriate tubing is used to allow the periodic filling of the measurement cell with an atmosphere identical to that in the reference cell.

8. We claim the microwave gas analyzer recited in claim 1 in which critical orifices are disposed upstream of the measurement and reference cells and are used in conjunction with a single vacuum pump to allow the measurement and reference cells to operate at equal, reduced pressures.

9. We claim the microwave gas analyzer recited in claim 1 in which the precision frequency for the phase-lock loop is derived from a Global Positioning System (GPS) receiver.

10. We claim the microwave gas analyzer recited in claim 1 in which the precision frequency for the phase-locked loop (PLL)is from a rubidium-cesium time base.

11. We claim the microwave gas analyzer recited in claim 1 in which the microwave energy is generated by a maser which utilizes the gas of interest for deriving its wavelength.

* * * * *